United States Patent [19]

Beech, Jr. et al.

[11] Patent Number: 5,288,924
[45] Date of Patent: Feb. 22, 1994

[54] PROCESS FOR STARTING UP AN OLEFIN HYDRATION REACTOR

[75] Inventors: James H. Beech, Jr.; Charles M. Sorensen, both of Wilmington, Del.; James A. Stoos, Blackwood, N.J.; Robert A. Ware, Wyndmoor, Pa.

[73] Assignee: Mobil Oil Corporation, Fairfax, Va.

[21] Appl. No.: 946,705

[22] Filed: Sep. 18, 1992

[51] Int. Cl.$^5$ .................. C07C 41/05; C07C 29/04
[52] U.S. Cl. ........................ 568/695; 568/897; 568/899; 568/697
[58] Field of Search ............ 568/695, 897, 899, 697

[56] References Cited

U.S. PATENT DOCUMENTS 4,783,555 11/1988 Atkins .
4,906,787 3/1990 Huang et al. .
5,012,014 4/1991 Child et al. .

Primary Examiner—Howard T. Mars
Attorney, Agent, or Firm—Alexander J. McKillop; Malcolm D. Keen; L. Gene Wise

[57] ABSTRACT

A method for starting up a fixed bed propylene hydration reactor containing shape selective metallosilicate catalyst particles for the production of isopropanol and/or diisopropyl ether is disclosed comprising the following sequential steps: contacting a feedstream comprising propane with catalyst particles in a hydration reactor; then introducing a feedstream comprising isopropanol into the reactor to displace propane. Next, a feedstream comprising propylene is introduced into the reactor under etherification conditions. Finally, a feedstream is introduced in the reactor comprising water under etherification and hydration reaction conditions whereby diisopropyl ether and isopropanol are produced.

24 Claims, No Drawings

PROCESS FOR STARTING UP AN OLEFIN HYDRATION REACTOR

This invention relates to a method for starting up an olefin hydration reactor containing a fixed catalyst bed. The invention particularly relates to a method for starting up a fixed bed reactor containing shape selective metallosilicate catalyst particles for the hydration of propylene to isopropanol (IPA) and etherification to provide high octane value diisopropyl ether (DIPE).

BACKGROUND OF THE INVENTION

Lower molecular weight alcohols and ethers such as isopropanol (IPA) and diisopropyl ether (DIPE) are in the gasoline boiling range and are known to have high blending octane numbers. In addition, by-product propylene from which IPA and DIPE can be made is usually available in a fuels refinery. An important aspect of research in the petroleum industry relates to processes to produce high octane lower aliphatic alkyl ethers as octane boosters and supplementary fuels.

The catalytic hydration of olefins, particularly $C_3$ and $C_4$ olefins, to provide alcohols and ethers is a well-established art. Representative olefin hydration processes are disclosed in U.S. Pat. Nos. 2,262,913; 2,477,380; 2,797,247; 3,798,097; 2,805,260; 2,830,090; 2,861,045; 2,891,999; 3,006,970; 3,198,752; 3,810,848; 3,989,762, among others.

Olefin hydration employing medium pore and large pore zeolite catalyst is a known synthesis method. As disclosed in U.S. Pat. No. 4,214,107 (Chang et al.), lower olefins, in particular propylene, are catalytically hydrated over a crystalline aluminosilicate zeolite catalyst having a silica to alumina ratio of at least 12 and a Constraint Index of from 1 to 12, e.g., acidic ZSM-5 type zeolite, to provide the corresponding alcohol, essentially free of ether and hydrocarbon by-product. Acid resin catalysts such as "Amberlyst 15" may also be used for hydration of light olefins.

The production of ether from secondary alcohols such as isopropanol and light olefins is known. As disclosed in U.S. Pat. No. 4,182,914, DIPE is produced from IPA and propylene in a series of operations employing a strongly acidic cationic exchange resin as catalyst. Recently, processes for the hydration of olefins to provide alcohols and ethers using zeolite catalyst such as ZSM-5 or zeolite Beta have been disclosed in U.S. Pat. Nos. 4,214,107 and 4,499,313 to Bell et al.; and U.S. Pat. Nos. 4,757,664, 4,857,664 and 4,906,187 to T. Huang. These patents are incorporated herein in their entirety by reference. One of the advantages in using zeolite catalyst for hydration and/or etherification of light olefins is the regenerability of the catalyst. Where resin based catalysts can decompose at the high temperatures required to remove deactivating amounts of carbonaceous deposits, zeolite catalysts remain thermally stable and can be regenerated oxidatively or in contact with hydrogen.

The hydration and etherification of lower olefins such as propylene to produce IPA and DIPE over a fixed bed of shape selective zeolite catalyst is generally carried out in liquid phase employing a feedstream comprising water and propylene at temperatures in excess of 200° F. and high pressure, preferably above 1000 psi. The maximum per pass conversion of propylene to DIPE is about 65 wt %. While attempting to maximize the rate of conversion, process conditions are selected to also reduce the more disadvantageous reactions which can occur during the process that could compromise the process advantages. These adverse reactions include the oligomerization of propylene, the formation of deactivating amounts of coke and carbonaceous deposits on the catalyst and the hydrothermal attack of water on the catalyst. These adverse reactions tend to find favor with increasing temperature and concentration providing a challenge to workers in the field to control reactor temperature, particularly at start-up when components may be present in high concentration.

In view of the foregoing problems relating to adverse reactions in the production of IPA and/or DIPE over fixed bed zeolite catalyst, starting up a hydration/etherification reactor is a particularly difficult problem. The fresh reactants, water and propylene, alone or in a mixture, exhibit high heats of adsorption on zeolite catalyst to the extent that on start up the fresh feed exotherm can cause severe local overheating of the catalyst bed. Hydrothermal attack by water on the catalyst destroys the structural integrity of the catalyst producing an excessive amount of generally ineffective fine particles. These fine particles are not only less catalytically effective but they complicate the subsequent removal of catalyst from the reactor. Propylene, added under typical start up conditions, can also experience local overheating providing conditions that promote unwanted oligomerization of propylene to produce undesirable by-product such as propylene dimer. These reactions of propylene can also lead to the formation of carbonaceous deposits on the catalyst and coke formation.

Starting up olefin hydration and etherification reactors containing fixed beds of zeolite catalyst present unique problems not encountered in commercial zeolite catalyzed conversion processes. Zeolite catalyzed processes such as the conversion of methanol to gasoline (MTG) or the oligomerization of olefins to higher hydrocarbons, the Mobil olefins to gasoline process (MOG), are vapor phase processes carried out at high temperature with feedstreams introduced as gases. Olefin hydration and etherification such as the zeolite catalyzed DIPE process are liquid phase processes that must be carried out at moderate temperatures and relatively high pressures. In the latter case, the likelihood of localized overheating and the consequent development of adverse side reactions during reactor start up are problems of substantial proportions that go beyond known commercial practice and have remained largely unresolved in the art heretofore.

Commercial start-up procedures for MTBE, methyl tertiary butyl ether, production where water is used to wet the catalyst would cause high temperature steaming for the DIPE system and lower activity due to water filled pores.

It is an object of the present invention to provide an improved process for the hydration of olefins using a fixed bed of zeolite catalyst particles.

It is a particular object of the present invention to provide a method for starting up an olefin hydration reactor containing a fixed bed of zeolite catalyst particles that avoids reactions deleterious to the efficacy of the catalyst.

A further objective of the invention is to provide an improved start up method for the zeolite catalyzed process for the conversion of propylene and water to IPA and/or DIPE.

SUMMARY OF THE INVENTION

A method has been discovered for starting up a reactor containing a fixed bed of metallosilicate catalyst particles employed in the liquid phase hydration of olefins to alkanol and etherification to dialkyl ethers. The method advantageously reduces the exotherm produced by the high heat of adsorption when water and/or olefin are employed directly in a reactor start up and thereby avoids damaging and deactivating the catalyst particles or producing undesirable byproducts of the reaction. It has been found that these advantages can be realized by initiating start-up using a feedstream comprising a readily liquefiable gas which is essentially inert as introduced into the reactor, has a high heat capacity but low heat of adsorption in contact with the catalyst. Lower paraffinic hydrocarbons are preferred. The paraffinic hydrocarbon is first contacted as a vapor which further reduces the sorption and heat release, reducing the problem with isopropanol and propylene reacting on start-up as the bed temperature increases due to sorption. The liquefied paraffinic hydrocarbon is displaced from the reactor with an alkanol feedstream whose heat of adsorption incrementally increases the temperature of the fixed catalyst bed. After the addition of alkanol, an olefin feedstream is introduced into the reactor which initiates a further incremental increase in bed temperature. Finally, water is introduced into the reactor, or a water/alkanol mixture, whereby olefin hydration occurs and steady state conditions are obtained for the production of alkanol and/or ether.

More particularly, a method for starting up a fixed bed propylene hydration reactor containing shape selective metallosilicate catalyst particles for the production of isopropanol and/or diisopropyl ether is disclosed comprising the following sequential steps: contacting a feedstream comprising propane with catalyst particles in a hydration reactor; then introducing a feedstream comprising isopropanol into the reactor to displace propane. Next, a feedstream comprising propylene is introduced into the reactor under etherification conditions. Finally, a feedstream is introduced in the reactor comprising water under etherification and hydration reaction conditions whereby diisopropyl ether and isopropanol are produced.

DETAIL DESCRIPTION OF THE INVENTION

The present invention is applicable to the conversion of individual light olefins and mixtures of olefins of various structures, preferably within the $C_2$–$C_7$ range, to alcohols and ethers. Accordingly, the invention is applicable to the conversion of ethylene, propylene, butenes, isobutylene, pentenes, isoamylenes, hexanes, and heptenes, mixtures of these and other olefins such as gas plant off-gas containing ethylene and propylene, naphtha cracker off-gas containing light olefins, fluidized catalytic cracker (FCC) light gasoline containing pentenes, hexanes and heptenes, refinery FCC propane/propylene streams, etc. However, the invention is particularly applicable to the hydration of propylene to IPA and etherification to produce diisopropyl ether (DIPE).

In the process to prepare DIPE a feedstock comprising propylene or a refinery $C_3$ hydrocarbon stream comprising olefins and paraffins, i.e., propylene and propane, is contacted at elevated pressure with an acidic catalyst and water as a reactant to hydrate propylene to form isopropanol (IPA) and DIPE. Minor amounts of oligomerization products of propylene are also formed in the acidic catalyst environment, particularly hexanes and nonenes. On a per pass basis, the conversion of propylene generally is about 50%, or between 30% and 70%. The effluent from the hydration and etherification zone is conventionally passed to a fractionator wherein a bottom stream is separated containing IPA and DIPE and an overhead stream that contains the unreacted $C_3$ hydrocarbons comprising propylene and propane, if an olefin and paraffin feedstock has been used. The $C_3$ stream, typically containing both propylene and propane, can be condensed and recycled to the pressurized DIPE reactor. The recycle stream may be fractionated to purify the propylene recycle. Conventionally, DIPE is recovered by distillation and/or extraction of the fractionator bottom stream. This recovery system also separates an IPA stream and a water stream. The IPA stream can be recycled to the etherification zone.

The operating conditions of the olefin hydration and etherification process include a temperature from about 60° to 450° C., preferably from about 130° to about 2200° C. and most preferably from about 140° to about 190° C.; a pressure of from about 100 (700 kPa) to about 3500 psi (24,500 kPa), preferably from about 1200 (8300 kPa) to about 2000 psi (14,000 kPa); a water to olefin mole ratio of from about 0.05 to about 30, preferably from about 0.1 to about 15 and most preferably from about 0.2 to about 3. For start-up operations, a temperature of between 250° F. (1210° C.) and 330° F. (1650° C.) is preferred.

The olefin hydration process can be carried out under dense phase, liquid phase, vapor phase or mixed vapor-liquid phase conditions in batch or continuous manner, preferably using a fixed bed reactor. Improved results are obtained with single dense phase or single liquid phase operation. A liquid hourly space velocity (LHSV) of from about 0.1 to about 20, preferably about 0.1–2, when operating continuously is suitable.

The catalyst employed in the olefin hydration and etherification operations is acidic resin catalyst such as sulfonated polystyrene or shape-selective acidic zeolite catalyst can be used. In general, the useful catalysts include zeolites Y, Beta, ZSM-35 and MCM-22. MCM-22 is described in U.S. Pat. No. 4,954,325 to Rubin, et al., incorporated herein by reference. Preferred catalysts include zeolite Beta and ZSM-35. Other catalysts effective for the hydration/etherification reaction include acidic medium and large pore shape selective zeolite catalyst particles, including ZSM-5, ZSM-11, ZSM-12, ZSM-22, ZSM-23, zeolite X, L, Y, USY, REY, Deal Y, ZSM-3, ZSM-4, ZSM-20, ZSM-50, mordenite and ferrierite.

ZSM-35 is more particularly described in U.S. Pat. No. 4,016,245, the entire contents of which are incorporated herein by reference.

Zeolite Beta is described in U.S. Pat. No. 28,341 (of original U.S. Pat. No. 3,308,069), to which reference is made for details of this catalyst.

Zeolite Y is described in U.S. Pat. No. 3,130,007, to which reference is made for details of this catalyst.

As noted above zeolites are effective catalysts for the conversion of olefins and water to alcohol and for reaction of alcohols and olefins to ethers. These reactions are typically operated under liquid phase or dense supercritical phase conditions at elevated temperature and pressure. Starting up a large fixed-bed reactor containing zeolite catalyst is difficult because direct contact between a liquid and an initially dry catalyst can cause high heat release due to adsorption of liquid in the zeolite pores. The initial heat release is compounded by heat release from exothermic reactions between the liquid feed components. The rapid heat release may cause physical breakup of catalyst extrudates into smaller particles. Catalyst disintegration can cause severe operational problems including poor catalyst performance, excessive fines formation, increase reactor pressure drop, disruption of reactant flow and distribution throughout the bed, and difficulties for catalyst unloading. In addition, the rapid temperature rise can cause temperature catalyst deactivation via coking.

The goals of start up in the present invention are to moderate the heat release by an initial contact with an inert vapor and fill the reactor with a benign liquid phase before pumping in the actual liquid reactant feed and before heating the reactor. The compound or composition used for start-up must be chemically inert towards the catalyst and not poison or damage it in any way. For zeolite olefin hydration catalysts, it has been shown that large excesses of either water or olefin co-reactant can damage the catalyst by two mechanisms as described herein before. Co-feeding both reactants at start up is also to be avoided because of the limited solubility of water and olefin at low temperatures, the possibility of multiple liquid phases contacting the catalyst and the reactive nature of these materials.

This invention discloses the use of hydrocarbon feedstreams comprising $C_3$-$C_{10}$ paraffins, individually or in a mixture, to start up an olefin hydration process in reactors containing fixed beds of zeolite catalyst. Hydrocarbon streams containing $C_3$-$C_5$ paraffin are preferred. Propane is particularly preferred. The propane is first administered as a low pressure gas to initiate heat release. Once the majority of heat is released, as evidenced by the progression of an exotherm through the catalyst bed, reactor pressure is increased above the liquefaction pressure. Liquid propane is recirculated through the bed and then displaced by pumping $C_1$-$C_4$ alcohol, or alkanol. Isopropanol is preferred. The alkanol may contain a minor amount of water but not enough to substantially increase the sorption exotherm. A small amount of additional heat is released by adsorption of the alcohol, without damage to the catalyst. At this point, olefins can be added, preferably propylene, and the reactor heated to reaction temperature. Once at temperature, pure alcohol can be replaced with water/alcohol reactant. The use of alcohol on start up is necessary to overcome the limited solubility of water and olefin. However, it is within the scope of this invention to replace or displace alcohol in the reactor in the start up procedure with water without adding additional alcohol at this point. The water/olefin hydration reaction which occurs upon water addition produces alcohol in situ which serves to augment the solubility of water in olefin.

An important aspect of the present invention is the order or sequence in which paraffinic hydrocarbon, alkanol, olefin and water are added to the reactor during start up. Preferably, that addition is in the order recited, namely: paraffinic hydrocarbon followed by alkanol, then followed by olefin, and finally followed by water or a water/alkanol mixture. Interchanging certain of the steps, particularly the addition of olefin before alkanol, results in the formation of olefin oligomers and rapid coke formation. Of course, adding significant amounts of water before or in conjunction with alkanol addition will accelerate hydrothermal attack on the catalyst with all the adverse consequences previously discussed. Basically, if the reactor were started up directly by feeding water, alcohol, and/or olefin directly, the catalyst would be damaged by excessive heat release, hydrothermal attack, and coking.

The following EXAMPLES are presented to illustrate the process of the invention and it's effectiveness.

EXAMPLE 1

The ability of a zirconia-bound zeolite Beta olefin hydration catalyst to resist disintegration by contact with liquids is qualitatively tested by dropping 1/16" extrudates into beakers containing various liquids including water, isopropanol, diisopropyl ether, and hexane. With water or isopropanol, the nominally dry catalyst breaks apart when contacted with the liquids. Based on visual observation, the severity of disintegration is ordered as follows:

$H_2O$ > Isopropanol > > Diisopropyl Ether ~ Hexene

This experiment demonstrates that excessive heat is generated by contact with liquid. Moreover, the catalyst in contact with liquid olefin turns brown indicating that coking of the catalyst is occurring.

EXAMPLE 2

A pilot plant consisting of three adiabatic reactors containing zirconia-bound zeolite Beta catalyst is started up by pulsing in gaseous propane at 10 psig (70 kPa) initial pressure and 70° F. (210° C). The extent of the exotherm is controlled to be below 150° F. (660° C.) . The location of the exotherm in the reactors is monitored by means of thermocouples positioned at fixed points down the axial length of the bed. The exotherm travels as a well defined front that moves progressively through the three beds over a period of 4 hours. During this time the total reactor pressure increases to 106 psig(742 kPa). once the exotherm has passed through, the pressure is increased to the liquefaction point for propane and then additional liquid propane is pumped in to raise the operating pressure to about 1500 psig (10,500 kPa). At this time the reactor pump-around system is started to recycle reactor effluent to the feed and essentially pure IPA is added to the reactor, accompanied by a slight exotherm. The pump-around is stopped and propane purged from the reactor with IPA. While continuing IPA addition, the pump-around is started and propylene addition to the reactor is started. The reactor temperature is raised gradually to about 275° F. (1350° C.) and the reactor feed is changed from essentially pure IPA to a mixture of about 65/35 weight percent IPA/Water at about 275° F. (1350° C.) . Next, the feedstream to the reactor is slowly raised to a temperature of about 290° F. (1430° C.) . At this juncture the start up operation is essentially complete and the reaction effluent can be passed to the extractor and distillation tower for product separation.

Catalyst from this experiment is both white, i.e.,low coke content, and is substantially unbroken. The catalyst has high activity for propene conversion.

In the present invention the reactor operating temperature once IPA/water addition has begun can be between 200° F. and 310° F. (93°-1540° C.) . However, the preferred operating temperature is between about 250° F. and 330° F. (121° C. and 1650° C.), with most preferred between 250°-275° F. (121°-1350° C.).

It is within the scope of this invention that the initial introduction of alkanol such as IPA to purge paraffins on start up can include a minor amount of water, generally less than 10 wt %, typically less than 1 wt %; but pure alkanol addition is preferred. Also, while it is preferred to feed a mixture of alkanol and water such as IPA/water to the reactor to establish the steady state hydration/etherification process following the alkanol purge step, water alone can be added without alkanol.

Moderating the wetting exotherm through the use of propane rather than water, IPA, or olefin is a major improvement demonstrated by the instant invention. Estimates of the adiabatic temperature rise for adsorption of water versus propane on zeolite Y have been calculated and compared in Table 1. The temperature increase for adsorption of water is significantly higher than that of propane; adsorption of isopropanol falls somewhere in between water and propane. An added complication with isopropanol is its dehydration to olefin and water which would be promoted by the elevated temperature and low partial pressures present during an IPA start-up. This reactivity results in catalyst coking by olefin oligomerization. Similar results in the ordering and magnitude of these exotherms are appropriate for intermediate and large pore zeolites including zeolite Beta.

TABLE 1

| Estimated Wetting Exotherms for Zeolite Y | |
|---|---|
| Sorbate | T (°F.) |
| Water | 520 (271° C.) |
| Propane | 125 (52° C.) |

Values for the heat of sorption are taken from the literature; sorbates uptakes were assumed to be 10 wt %, and a catalyst heat capacity of 0.3 BTU/lb °F. was used (Literature reference: *Zeolite Molecular Sieves*, D. W. Breck, John Wiley & Sons, N.Y., 1974).

The start-up procedure of the present invention can be applied to any zeolite-based catalytic process that involves the use of polar reactants such as water, alcohols, amines, olefins, etc. Applicable processes include, but are not limited to: olefin hydration to alcohols such as ethylene to ethanol, propylene to isopropanol and butylenes to butanols, olefin etherification processes such as MTBE, TAME, and FCC gasoline ethers, alcohol to gasoline (i.e. MTG), amination reactions such as propylene and ammonia to propyl amine.

In general, the invention comprises a process for controlling the start-up exotherm of an adiabatic fixed bed reactor containing shape selective metallosilicate catalyst particles employed for the liquid phase conversion of one or more convertible fresh reactants, which reactants produce a catalyst deactivating exotherm when freshly placed in contact with the catalyst. Overall, the process comprises the sequential steps of introducing into the reactor a feedstream comprising a liquefiable vapor composition that is essentially unreactive in contact with the catalyst. The pressure of the reactor is then increased above the liquefaction pressure of the vapor composition and a liquid feedstream comprising the liquid phase corollary of the composition is introduced. The liquid feedstream is displaced from the reactor with a liquid feedstream comprising one or more of the convertible fresh reactants under conversion conditions.

While the invention has been described by reference to specific embodiments, there is no intent to limit the scope of the invention except as described in the following claims.

What is claimed is:

1. A method for controlling the catalyst deactivating start up exotherm of an adibatic fixed bed reactor containing shape selective metallosilicate catalyst particles for $C_3-C_7$ olefinic hydrocarbon liquid phase hydration and etherification, comprising in sequence:
    a) introducing into said reactor a feedstream comprising $C_3-C_{10}$ paraffinic hydrocarbon vapor in contact with said particles;
    b) increasing the pressure of said reactor above the liquification pressure of step (a) vapor and passing liquid $C_3-C_{10}$ paraffinic hydrocarbon into said reactor;
    c) displacing step (b) liquid hydrocarbon from said reactor with a feedstream comprising alkanol;
    d) introducing a feedstream comprising said $C_3-C_7$ olefinic hydrocarbon into said reactor containing said alkanol;
    e) introducing a feedstream comprising water into said reactor containing said olefinic hydrocarbon under etherification and hydration reaction conditions.

2. The process of claim 1 wherein said hydrocarbon feedstream comprises $C_3-C_5$ paraffinic hydrocarbons.

3. The process of claim 1 wherein said hydrocarbon feedstream comprises propane.

4. The process of claim 1 wherein said alkanol comprises $C_1-C_4$ alkanol.

5. The process of claim 1 wherein said alkanol comprises isopropanol.

6. The process of claim 1 wherein said olefinic hydrocarbon feedstream comprises propylene.

7. The process of claim 1 wherein said shape selective metallosilicate catalyst particles comprise aluminosilicate particles.

8. The process of claim 7 wherein said aluminosilicate particles comprise zeolite selected from the group consisting of ZSM-5, ZSM-11, ZSM-12, ZSM-22, ZSM-23, ZSM-35, zeolite X, L, Y, USY, REY, Deal Y, ZSM-3, ZSM-4, ZSM-20, ZSM-50, MCM-22, zeolite Beta, mordenite and ferrierite.

9. The process of claim 1 wherein step (e) etherification and hydration conditions comprise temperature between 200°–360° F. (93°–1820° C.), pressure of from about 100 (700 kPa) to about 3500 psi (24,500 kPa) and a water to olefin mole ratio of from about 0.05 to about 30.

10. The process of claim 9 wherein said temperature is between 250° F. (121° C.) and 330° F. (1650° C.).

11. The process of claim 1 wherein step (c) alkanol feedstream contains a minor amount of water.

12. The process of claim 1 wherein step (e) water feedstream contains alkanol.

13. A method for controlling the start up exotherm of an adibatic fixed bed propylene hydration and etherification reactor containing shape selective metallosilicate catalyst particles for the production of isopropanol and diisopropyl ether, said method consisting essentially of the following sequential steps:
    a) contacting a feedstream comprising propane vapor with said particles in said reactor;
    b) increasing the pressure of said reactor above the liquification pressure of said vapor and passing liquid propane into said reactor;
    c) introducing a feedstream comprising isopropanol into said reactor to displace step (b) liquid propane;

d) introducing a feedstream comprising propylene into said reactor containing said isopropanol;

e) introducing a feedstream comprising water into said reactor under etherification and hydration reaction conditions comprising temperature between 200°–360° F. (93°–182° C.), pressure of from about 100 (700 kPa) to about 3500 psi (24,500 kPa) and a water to olefin mole ratio of from about 0.05 to about 30 whereby diisopropyl ether and isopropanol are produced.

14. The process of claim 13 wherein step (c) isopropanol feedstream contains a minor amount of water.

15. The process of claim 13 wherein step (e) water feedstream contains isopropanol.

16. The process of claim 13 wherein said metallosilicate particles comprise aluminosilicate zeolite particles selected from the group consisting of ZSM-5, ZSM-11, ZSM-12, ZSM-22, ZSM-23, ZSM-35, zeolite X, L, Y, USY, REY, Deal Y, ZSM-3, ZSM-4, ZSM-20, ZSM-50, MCM-22, zeolite Beta, mordenite and ferrierite.

17. The process of claim 13 wherein said temperature is between 250° F. (121° C.) and 330° F. (165° C.).

18. In the process for the liquid phase production of isopropanol and diisopropyl ether comprising contacting an adibatic fixed bed of shape selective zeolite catalyst particles in a reactor with a feedstream containing propylene and water under propylene hydration and etherification conditions, the improvement comprising:

initiating said process by introducing a feedstream comprising propane vapor into said reactor; then increasing the pressure of said reactor above the liquification pressure of said vapor and passing liquid propane into said reactor; next, displacing said liquid propane with a feedstream comprising isopropanol; then introducing a feedstream comprising propylene into said reactor containing said isopropanol; then introducing a feedstream comprising water into said reactor under said etherification and hydration reaction conditions whereby said diisopropyl ether and isopropanol are produced.

19. The process of claim 18 wherein said feedstream comprising isopropanol also contains a minor amount of water.

20. The process of claim 18 wherein said feedstream comprising water also contains isopropanol.

21. The process of claim 18 wherein said shape selective zeolite catalyst particles comprise particles selected from the group consisting of ZSM-5, ZSM-11, ZSM-12, ZSM-22, ZSM-23, ZSM-35, zeolite X, L, , USY, REY, Deal Y, ZSM-3, ZSM-4, ZSM-20, ZSM-50, MCM-22, zeolite Beta, mordenite and ferrierite.

22. A process for starting up a fixed bed reactor containing shape selective metallosilicate catalyst particles for liquid phase hydration and etherification of propylene to produce isopropanol and diisopropyl ether, comprising in sequence:

a) introducing into said reactor a vapor feedstream comprising $C_3$–$C_{10}$ paraffinic hydrocarbon in contact with said particles;

b) increasing the pressure of said reactor above the liquefication pressure of said vapor and passing liquid $C_3$–$C_{10}$ paraffinic hydrocarbon into said reactor;

c) displacing said liquid hydrocarbon from step (b) reactor with a feedstream comprising isopropanol;

d) introducing a hydrocarbon feedstream comprising propylene into step (c) reactor containing said isopropanol;

e) introducing a feedstream comprising water into step (d) reactor containing said propylene under etherification and/or hydration reaction conditions.

23. The process of claim 22 wherein said $C_3$–$C_{10}$ paraffinic hydrocarbon feedstream comprises propane.

24. The process of claim 22 wherein step (e) etherification and hydration conditions comprise temperature between 200°–360° F. (93°–182° C.), pressure of from about 100 (700 kPa) to about 3500 psi (24,500 kPa) and a water to olefin mole ratio of from about 0.05 to about 30.

* * * * *